United States Patent [19]

Brånemark

[11] Patent Number: 5,725,581
[45] Date of Patent: Mar. 10, 1998

[54] ANCHORING ELEMENT SUPPORTING PROSTHESES OR A JOINT MECHANISM FOR A RECONSTRUCTED JOINT

[75] Inventor: Per-Ingvar Brånemark, Molndal, Sweden

[73] Assignee: Medevelop AB, Sweden

[21] Appl. No.: 757,901

[22] Filed: Nov. 27, 1996

Related U.S. Application Data

[63] Continuation of Ser. No. 549,910, Oct. 30, 1995, abandoned, which is a continuation of Ser. No. 145,071, Oct. 27, 1993, abandoned.

[30] Foreign Application Priority Data

Oct. 29, 1992 [SE] Sweden .................. 92 03 181-4

[51] Int. Cl.$^6$ .................. A61F 2/28; A61B 17/86
[52] U.S. Cl. .................. 623/16; 606/73; 411/421; 411/386
[58] Field of Search .................. 411/395, 411, 411/418, 420–422; 433/174; 606/73, 72, 67; 623/17, 18, 16

[56] References Cited

U.S. PATENT DOCUMENTS

| | | | |
|---|---|---|---|
| 45,133 | 11/1864 | Bonwill | 411/421 |
| 1,232,099 | 7/1917 | Schoenert | 408/222 |
| 1,708,793 | 4/1929 | Jones | 411/421 X |
| 2,165,011 | 7/1939 | Rosenberg | 411/420 |
| 2,387,720 | 10/1945 | Davis | 411/418 X |
| 3,240,102 | 3/1966 | Sandor | 411/418 |
| 3,911,781 | 10/1975 | Bappert | 411/418 |
| 4,537,185 | 8/1985 | Stednitz | . |
| 4,712,957 | 12/1987 | Edwards et al. | 411/82 |
| 4,861,206 | 8/1989 | Riedel | 411/36 |
| 4,927,421 | 5/1990 | Goble et al. | 606/73 |
| 5,013,313 | 5/1991 | Surer | 606/60 |
| 5,108,443 | 4/1992 | Branemark | . |
| 5,195,891 | 3/1993 | Sulc | 433/173 |
| 5,222,847 | 6/1993 | Hiyama et al. | 408/222 |

FOREIGN PATENT DOCUMENTS

| | | | |
|---|---|---|---|
| 230856 | 8/1987 | European Pat. Off. | 606/73 |
| 0454646 | 4/1991 | European Pat. Off. | . |
| 3027138 | 12/1981 | Germany | . |
| 8803007 | 5/1988 | WIPO | 433/174 |
| 9001303 | 2/1990 | WIPO | 433/174 |

Primary Examiner—David H. Willse
Attorney, Agent, or Firm—Ostrolenk, Faber, Gerb & Soffen

[57] ABSTRACT

An anchoring element (1) for supporting prostheses or part thereof. The anchoring element (1) is substantially rotationally symmetrical and provided with external threads (20) and a central bore (2). At least one slit (3, 4, 5, 6) is arranged in spiral form around the longitudinal axis (13) of the element (1) and extends over at least the major part (11, 12) of the outer wall of the element. The major part is provided with external threads (20), the chirality of the slit (3, 4, 5, 6) being the same as that of the outer threads (20).

17 Claims, 2 Drawing Sheets

ANCHORING ELEMENT SUPPORTING PROSTHESES OR A JOINT MECHANISM FOR A RECONSTRUCTED JOINT

This is a continuation of application Ser. No. 08/549,910, filed on Oct. 30, 1995, now abandoned, which is a continuation of application Ser. No. 08/145,071, filed on Oct. 27, 1993, now abandoned.

BACKGROUND OF THE INVENTION

The present invention relates to an anchoring element for supporting a prosthesis, the anchoring element having essentially the form of a screw and being arranged for connection by its outer end portion to the prothesis and by its opposite inner end portion to be inserted and anchored in bone tissue.

The invention can also be used for supporting a joint mechanism, but is preferably used in reconstructions after amputations or other defects.

DESCRIPTION OF THE RELATED ART

Anchoring of prostheses in bone tissue by anchoring elements having essentially the form of a screw is known in the art. Excellent results have been obtained in respect of osseointegration of such implant elements and their preserved function with dental prostheses anchored in the jaw bone by fixtures according to a method developed by professor Branemark and co-workers. In addition to fixture design, non-traumatic surgery techniques and properties of fixture material and surface have been of importance in this respect.

For reconstruction of joints U.S. Pat. No. 5,171,284 proposes a rotationally symmetric, at least partially hollow anchoring element for reconstruction of joints, particularly for reconstruction of finger joints. This known anchoring element has essentially rotationally symmetric form and is provided with external threads on the major part of its outside and arranged for connection at its outer end portion to the prosthesis or parts thereof, and for insertion and anchoring in bone tissue by its opposite inner end portion, wherein at least one slit with cutting edges extends from the inner end of the anchoring element in direction of the outer end portion of the element. The mantle surface of the known anchoring element may have holes that are advantageously formed like cutting edges. These features make the fixture anchorable, there being no need to provide the hole drilled into bone tissue with threads, i.e. the fixture is self-tapping. This further reduces the trauma caused during implantation, resulting in promotion of the integration by the healing process. The bone material removed by ablation in the tapping process is received by the slits or cavities and is restructured or resorbed by-and-by.

This known anchoring element has however been designed for anchoring of small joints, particularly finger joints; in this context, the bore in which the fixture is to be secured by screwing is arranged in a hole made in the longitudinal direction of the bone. In such case the amount of bone material removed by tapping is comparatively small.

The self-tapping properties of such a fixture may however be further improved, particularly if the fixture is intended to be used for larger joints, for self-tapping in dense bone tissue or at a larger depth of fixation, in which case the bone material removed by tapping will have a larger volume for which sufficient space has to be provided in cavities or slits of the fixture.

OBJECTS OF THE INVENTION

It is the principle object of the invention to provide an anchoring element of the type described in the introduction, which does not have these drawbacks and which is, i.a., designed to allow for communication and through-growth of vessels, bone marrow, etc. to eliminate the risk of bone atrophy, i.e. the bone withering away.

SUMMARY OF THE INVENTION

According to the present invention an anchoring element is defined which is provided with a central through bore and having a slit or slits arranged in spiral form around the longitudinal axis of the anchoring element and extending over the major part of the threaded outside provided with external threads, the spirality of the slit being the same as that of the external threads.

According to a preferred aspect of the invention the wall thickness of the anchoring element is progressively decreasing over a portion near the inner end and in a direction towards the inner end.

According to a further aspect of the invention a bridge of material is arranged between the slit walls and along a slit portion extending from the closed end of the slit, the bridge of material being penetrated by at least one hole, the inner wall of the bridge being delimited by the centred bore and the thickness of the bridge in a radial direction being substantially smaller than the radial wall thickness of the portion of the element bordering the portion of the slit provided with bridges.

It is preferred for the lateral walls of the slit to be plane-parallel to each other and for the hole or holes penetrating the bridge of material to be circular, the diameter of the holes being substantially similar to the slit width.

According to another advantageous aspect of the invention the central bore widens in the direction of the inner end of the element. Preferably the widening of the bore is substantially conical. It is preferred for the anchoring element to lack bridges bridging the spiral slits in its portion widening in the direction of the inner end of the element.

According to a third advantageous aspect of the invention the inner end of the element has the form of an intersected annular edge, the radius of which substantially corresponds to the inner diameter of the exterior threads.

According to a preferred embodiment the number of spiral slits is two or three or a multiple of two; if the number is two or a multiple of two the slits in each pair are arranged opposite to each other in respect of the center bore axis; in all intersectional planes perpendicular to the axis neighboring slits are equidistant from each other. In this connection it is preferred for the area occupied by slits in the portion of the anchoring element provided with slits to be between 15 and 50%. The ratio between the pitch of the exterior threads and the pitch of each spiral slit is between 20:1 and 500:1, preferably about 100:1.

It is furthermore preferred for the outer wall portion bordering the inner end to lack threads but to have been appropriately coarsely worked in a lathe, and for the inner portion of the anchoring element to be somewhat radially resilient. Preferably the fixation means for a prosthesis or a part of a prosthesis comprises internal threads and/or a hexagonal portion arranged at the outer end portion of the anchoring element.

It is also preferred for the element to have a bore in its outer end portion, the bore being tilted in respect of the center axis by an angle β of between 25° and 65° to provide for passage of a nerve or a feeding means or for a sinew or for external communication.

At least in its parts being in contact with tissue upon implantation the anchoring element is preferably of titanium or another tissue-friendly material, and is provided, at least in regard of the portion of its surface having contact with tissue upon implantatiom, with a micropitted surface, the pit diameter being between 10 and 1 000 nm, preferably between 10–300 nm.

The anchoring element according to the invention is intended for use in securing prostheses or parts thereof in bone tissue or for external communication or transmission of biologic and physical parameters.

The invention also discloses a method for anchoring an anchoring element for prostheses or parts of prostheses in bone tissue, the anchoring element having a hollow center and being provided with external threads and self-tapping means, the process comprising production of a hole in bone tissue, the diameter of the hole approximately corresponding to the inner diameter of the external threads of the anchoring element, the hole having a length adapted to the insertion depth of the element, insertion of the element into the hole by self-tapping screwing-on while removing bone material by ablation and thereby forming threads in the bone material, the threads corresponding to the external threads of the anchoring element, whereby the removed bone material is received by one or several grooves provided in the outer wall of the anchoring element and is transported in the grooves in the direction of the outer end portion of the anchoring element, and anchoring the element in the bone by cooperation of its external threads with the threads cut into the bone tissue, fixation of a prosthesis or a part of a prosthesis to the outer end of the anchoring element, the fixation being carried out in direct connection with the implantation of the element or a short time thereafter. It is also preferred for the method to further comprise post-implantation supply of pharmacologically active agents, such as agents promoting integration by the healing process and bactericides, the supply being fed through the symmetrically centered bore of the anchoring element to the bone tissue area provided with the hole for implantation of the element.

BRIEF DESCRIPTION OF THE DRAWINGS

The invention will be described in more detail in the following with reference to the accompanying drawings relating to a preferred but not limiting embodiment.

The drawings are not drawn to scale and only approximate dimensional relationships.

Figure 1:
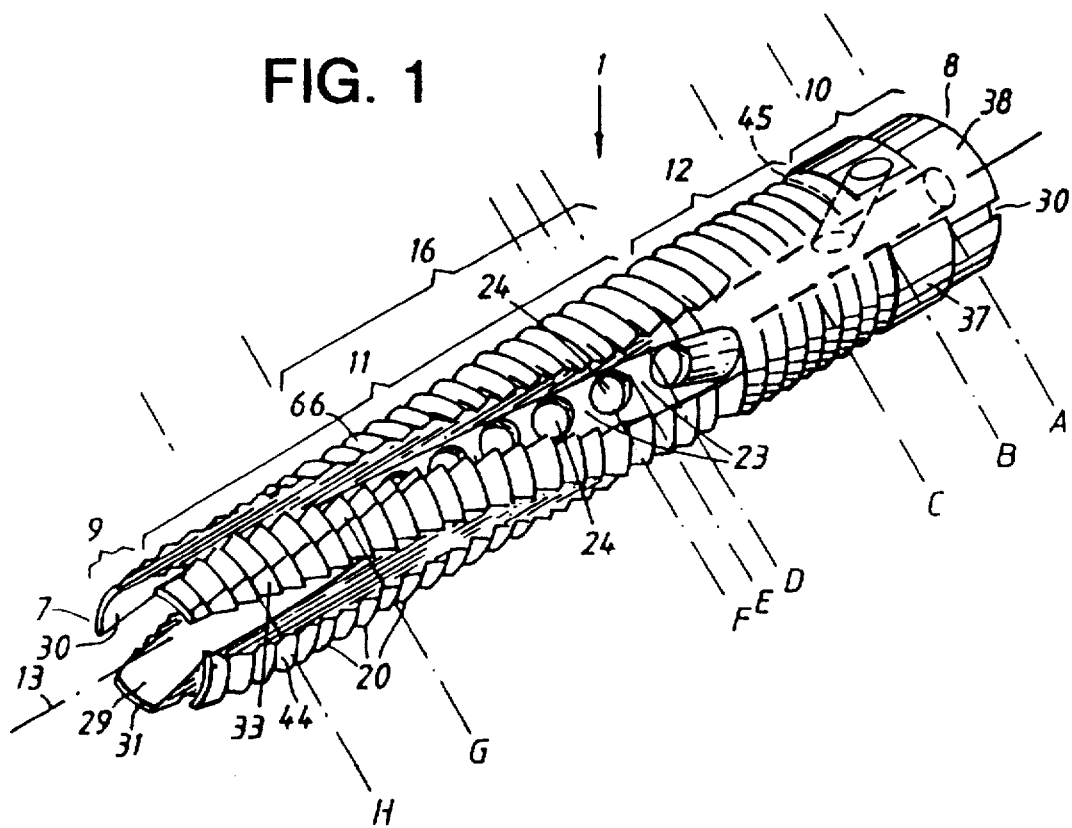
FIG. 1 shows an anchoring element constructed according to the invention, in an oblique side view and in perspective.
Figure 2:
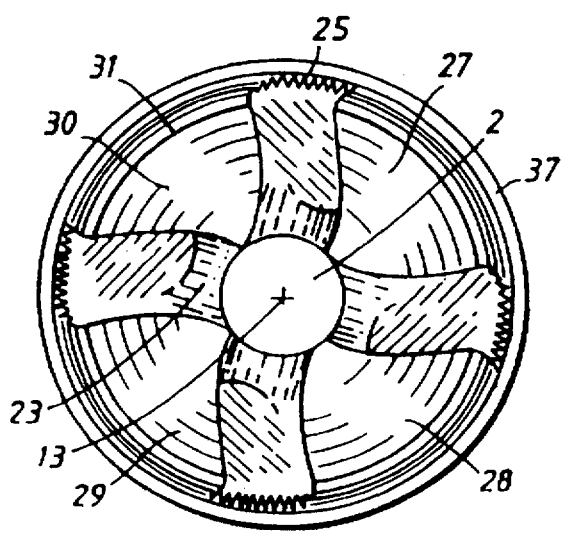
FIG. 2 shows an end view of the element or object in FIG. 1, in a direction towards the inner end, FIG. 3 snows an end view of the object in FIG. 1, in a direction towards the outer end.
Figure 3:
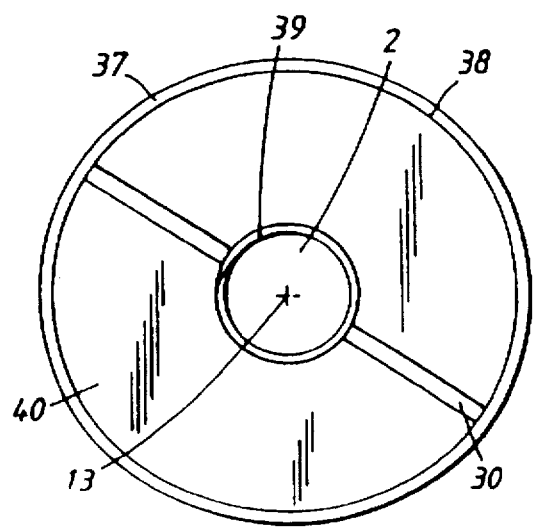
Figure 4A:
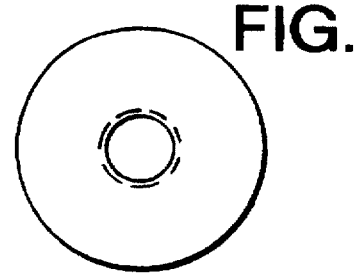
FIGS. 4A through 4H are sections perpendicular to the rotational axis of the anchoring element or object in FIG. 1 taken through the respective lines A through H.
Figure 4B:
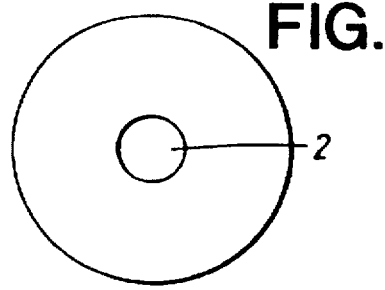
Figure 4C:
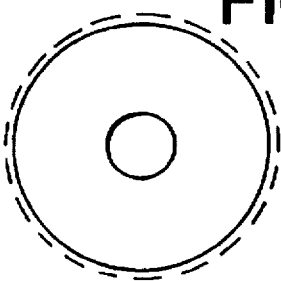
Figure 4D:
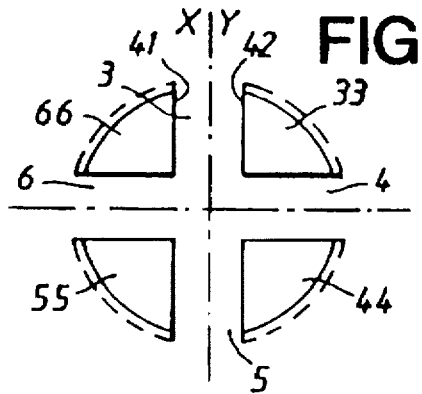

The anchoring element 1 according to the invention shown in FIG. 1 is constructed of pure titanium that had been worked in a lathe and has the approximate shape of a cylindrical sleeve with a symmetrically centered through bore 2. On its outside the mantle of the cylindrical sleeve is provided with threads 20 commencing adjacent to inner end 7, and extending toward the other or outer end 8, said threads 20 covering the major part of the mantle, except for a narrow zone 9 having a width of about one thread pitch and a comparatively wider zone 10 adjacent to outer end 8. The portion of the cylinder mantle provided with outer threads comprises two sections, one non-segmented section 12 (shown in FIG. 4C) bordering the wider outer end zone 10, and a section 11 divided into four segments in the longitudinal direction of the element (shown in FIGS. 4D to 4H) extending between the non-segmented section 12 and the narrow inner end zone 9 segmented in the same way as segmented section 11.

Segmentation of the inner end zone 9 and the section 11 bordering thereon into four segments 33, 44, 55, 66 about circular in transaction is due to four slits 3, 4, 5, 6 dissecting the cylinder wall and communicating with center (central) bore 2. Slits 3, 4, 5, 6 have spiral form and are symmetrically positioned in respect of the centre axis 13 of the cylinder bore and have parallel side walls 41, 42 and open ends coinciding with the inner end 7 of the element. Slits 3, 4, 5, 6 are closed at their other ends defined by the border between segmented portion 11 and non-segmented portion 12. The ratio of pitch of slits 3, 4, 5, 6 to pitch of exterior threads 20 is about 100:1, each of slits 3, 4, 5, 6 corresponding to a fourth of a full thread (thread segment of 90°; rotational angle α in FIG. 4). Rotation of slits 3, 4, 5, 6 and thus of segments 33, 44, 55, 66 thus is plainly evident from the sections in FIG. 4D–4H.

Figure 4E:
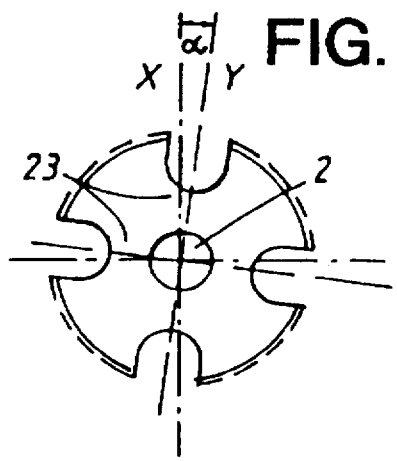
Figure 4F:
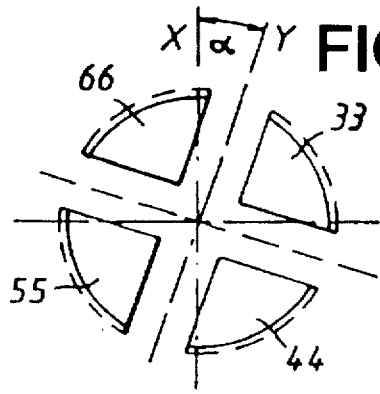
Figure 4G:
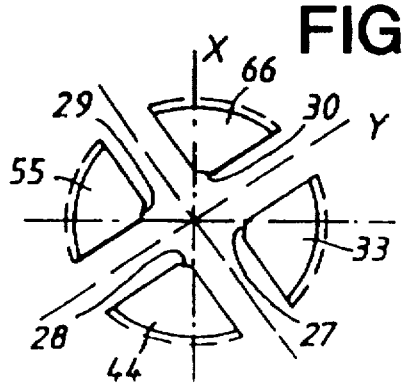
Figure 4H:
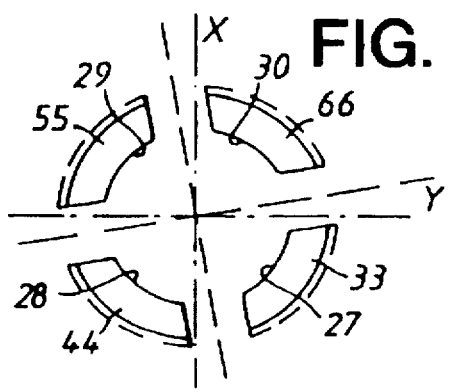

Segmentation of anchoring element 1 is complete only in one portion extending from the inner end 7 in direction of the outer end 8 and bordering a partially segmented portion 16 (shown in FIG. 4D, 4E, 4F) comprising the remaining part of the segmented section. The partial segmentation is due to material bridges 23 (section through such a bridge is shown in FIG. 4E) connecting segments 33, 44, 55, 66 and which, in respect of center axis 13, extends from bore 2 outwards in radial direction, having a thickness in this direction of about a fourth of the radial thickness of the threaded cylinder wall of anchoring element 1 near bridges 23. Each bridge 23 is segmented by circular holes (shown in section in FIG. 4D, 4F) with a diameter corresponding to the width of slits 3, 4, 5, 6. Alternatively, the holes can have another shape, e.g. an oval shape. The slit portions provided with bridges 23 thereby assume the shape of spiral notches or grooves. Groups of four holes 24, one each for each slit 3, 4, 5, 6, are arranged in the same plane perpendicular to center axis 13. For reasons of comprehensiveness, only material bridge 23 connecting segments 33 and 66 is shown in FIG. 1.

Bore 2 of anchoring sleeve 1 widens conically (shown in section in FIG. 4G, 4H) towards the inner end 7 under formation triangular cone mantle segments 27, 28, 29, 30, the bases of which coincide with a segmented circular inner end edge 31 formed by intersection of the cone by the outer wall of the cylinder mantle. In a section near inner end 7 the outer mantle is bevelled, such as to make the axial width of external threads 20 to successively decrease in direction towards the inner end 7; the section comprises the aforementioned narrow zone 9 near the inner end 7 and some further outer threads 20.

Dissection of slits 3, 4, 5, 6 by outer threads 20 is such as to form sharp edges or rims 25 causing ablation of bone shavings during screwing-on. The material removed by ablation is received by the cavity formed by the conical widening at inner end 7 and by slits 3, 4, 5, 6. By arranging slits 3, 4, 5, 6 with the same direction of spiral rotation—directional spirality—as outer threads 20, the bone shavings in slits 3, 4, 5, 6 are transported in the direction of outer end 8 of element 1 during screwing-on of the anchoring element. This avoids tissue compression and local accumulation of material. By reason of the wall thickness near inner end 7 being comparatively small a certain spring action is obtained in radial direction; this facilitates screwing-on and, at the same time, decreases the stress at the inner end, particularly at functional loads. Bridges 23 conteract deformation in tangential direction of anchoring element segments 33, 44, 55, 66 and thereby safeguard the self-tapping function, whereas, at the same time, holes 24 between bridges provide communication between bore 2 and slits 3, 4, 5, 6 facing the free bone wall.

This communication is of importance, i.a., if factors promoting ingrowth of tissue or antibiotics are to be introduced from the outer end through bore 2 after implant of the element. Anchoring after integration by the healing process is also strengthened and a communication channel for bone marrow and anchoring bones is obtained.

The wide zone 10 of anchoring element 1, lacking threads and located adjacent to outer end 8 of element 1 has an annular flange 37 (shown in section in FIG. 4B) bordering the threaded but not segmented mantle portion 12, and an end portion 38 (shown in section in FIG. 4A) with reduced diameter bordering ring flange 37. In a portion extending from outer end 8 in direction of inner end 7 bore 2 is provided with internal threads 39 for fixation of a prosthesis or a part of a prosthesis. A slot 30 in the outer end wall 40 serves for screwing-on of anchoring element 1 and as a counterstay if a prosthesis or a part of a prosthesis is to be mounted on element 1, for example by screwing-on a screwing means of the prosthesis or the prosthesis element into internal threads 39. For the rest the outer end of the anchoring element is designed in a traditional way to obtain optimal fixation of the prosthesis or prosthetic element. Extending between central bore 2 and the outside of anchoring element 1 at an angle of between 25° and 65° is tilted bore 45. The latter provides a passage for a nerve, or a feeding means, or a sinew, or may be used for external communication.

Slits with circular geometry and thus deeply cut into the material are appropriately arranged in the inner portion of the fixture the further outwards one is moving (if a greater extent of stiffness is desired), since the circles can be moved towards the periphery.

Implantation of the anchoring element 1 proposed according to the invention may, for instance, be carried out in the following way:

In surgical implantation of the anchoring element a hole is made in the bone selected as an anchoring site by use of a drill having essentially the same diameter as inner diameter 20 of the exterior threads, the hole being made to a depth that is somewhat, but not much, larger than the distance between inner end 7 of element 1 and ring flange 37. Thereafter the anchoring element 1 is screwed into the bore while simultaneously removing bone material by ablation and formation of threads in the bone material. Anchoring element 1 is allowed to be integrated by the healing process during a period of time of from 2 to 6 months to achieve permanent anchoring, i.e. osseointegration. Thereafter the outer end of anchoring element 1 is exposed and a prosthesis (not shown) or part of a prosthesis is mounted thereon. The prosthesis so mounted will be able to bear loads right from the start.

I claim:

1. An essentially rotationally symmetric one piece anchoring element for supporting a prosthesis or parts thereof, said anchoring element including:

a central bore extending longitudinally through said element;

a generally cylindrical outer surface;

an inner end portion at a first end of said element;

an outer end portion at a second end of said element opposite said first end;

external threads spiraling around said bore and extending over a major portion of said outer surface, and at least one open slit extending from said inner end portion toward said outer end portion, and extending from said outer surface to said central bore;

said outer end portion being operatively constructed for connection with said prosthesis or parts thereof;

said inner end portion being operatively constructed for insertion and anchoring in bone tissue;

said slit being of a spiral form with respect to said bore and extending lengthwise over a major lengthwise part of said outer surface, said external threads extending over at least said major lengthwise part;

said slit being of a first pitch and said external threads being of a second pitch, said first pitch being substantially greater than said second pitch;

said slit being provided with cutting edges for cutting bone tissue by rotating said anchoring element as said inner end portion is inserted into a hole in said bone tissue; and also said slit having directional spirality which is the same as directional spirality of said external threads.

2. The anchoring element as claimed in claim 1, wherein wall thickness of the element progressively decreases over a portion near the first end and in a direction towards the first end.

3. The anchoring element as claimed in claim 1, wherein each one slit is defined by spaced walls and wherein a bridge of material is arranged between a walls or the slit and along a slit portion extending from a closed end of the slit, said bridge of material being penetrated by at least one hole, said bridge including an inner wall that is delimited by the central bore and the thickness of the bridge of material being substantially smaller than a wall thickness of the portion of the element extending in radial direction from the bridge of material.

4. The anchoring element as claimed in claim 3, wherein said spaced walls of the slit are plane-parallel with respect to each other and that each hole of the at least one hole penetrating the bridge of material is substantially circular, with a diameter substantially similar to a width of the slit.

5. The anchoring element as claimed in claim 1, wherein the central bore of the element widens in direction of the first end of the element.

6. The anchoring element as claimed in claim 5, wherein the widening of said central bore is substantially conical.

7. The anchoring element as claimed in claim 5, wherein the anchoring element lacks a bridge between each spiral slit in the portion widening in direction of the first end of the element.

8. The anchoring element as claimed in claim 1, wherein the inner end portion of the element has the form of an intersected annular edge, the diameter of which substantially corresponds to an inner diameter of the external threads.

9. The anchoring element as claimed in claim 1, wherein said at least one slit includes at least two slits.

10. The anchoring element as claimed in claim 9, wherein said slits comprise at least one pair of slits arranged opposite to each other with respect to a central bore axis, wherein all slits positioned adjacent to each other are equidistant in all intersectional planes perpendicular to said axis.

11. The anchoring element as claimed in claim 10, wherein a portion of the anchoring element is provided with slits and has an overall area, and wherein an area of the slits in said portion of the anchoring element which is provided with slits is between 15 and 50% of said overall area.

12. The anchoring element of as claimed in claim 1, wherein a section of the outer surface bordering the inner end portion lacks external threads.

13. The anchoring element as claimed in claim 1, wherein said inner end portion is somewhat radially resilient.

14. The anchoring element according to claim 1, wherein fixation means for a prosthesis or a part of a prosthesis comprises internal threads arranged in the central bore at the outer end portion of the anchoring element.

15. The anchoring element according to claim 1, wherein the element also includes another bore in said outer end portion, said another bore tilting in respect of a central bore axis by an angle B of between 25° and 65° to provide for passage of a nerve or a feeding means from said central bore to a point outside of said element at said outer end portion.

16. The anchoring element according to claim 1, wherein the ratio between the pitch of said external threads and the pitch of each spiral slit is between 20:1 and 500:1.

17. The anchoring element according to claim 1, wherein the element, at least in parts to be in contact with tissue upon implantation, is of a biocompatible material and has a micropitted surface with a pit diameter of between 10 and 1 000 nm.

* * * * *